United States Patent [19]

Knapp

[11] Patent Number: 4,775,319
[45] Date of Patent: Oct. 4, 1988

[54] DENTAL CORE FORM AND METHOD OF USE

[76] Inventor: Mark W. Knapp, 17 Melville Rd., West Brunswick, Australia

[21] Appl. No.: 883,721

[22] Filed: Jul. 9, 1986

Related U.S. Application Data

[63] Continuation-in-part of Ser. No. 751,740, May 28, 1985, abandoned.

[30] Foreign Application Priority Data

Sep. 14, 1984 [WO] PCT Int'l Appl. .................. PCT/AU84/00180

[51] Int. Cl.[4] .............................................. A61C 9/00
[52] U.S. Cl. ...................................... 433/40; 433/223
[58] Field of Search ................... 433/40, 39, 213, 219, 433/223

[56] References Cited

U.S. PATENT DOCUMENTS 2,154,499  4/1939  Eisenstein ........................... 433/219
2,878,565  3/1959  Schwartz .............................. 433/40
2,958,946  11/1960  Chertkof ............................... 433/40
3,304,608  2/1967  Frohnecke ............................ 433/40
3,318,001  5/1967  Rubin .................................... 433/40
3,686,754  8/1972  Kondoloff ........................... 433/223
4,253,829  3/1981  Adelberger .......................... 433/40
4,424,034  1/1984  Korwin et al. ....................... 433/40
4,459,112  7/1984  Shoher et al. ..................... 433/223

FOREIGN PATENT DOCUMENTS 721974  6/1942  Fed. Rep. of Germany ........ 433/39

Primary Examiner—John J. Wilson
Attorney, Agent, or Firm—Antonelli, Terry & Wands

[57] ABSTRACT

A dental core form including a sleeve-like member to fit on a portion of a tooth on which a core for a crown is to be formed. The form is corrugated longitudinally and made of synthetic plastic material. Stippling or roughening of the lower part on the outside of the form will assist to secure the form by adhesive in the mouth during formation of the core.

6 Claims, 3 Drawing Sheets

DENTAL CORE FORM AND METHOD OF USE

This is a continuation-in-part application of Ser. No. 751,740, filed May 28, 1985, now abandoned.

This invention relates to an improved method of and means for making cores for dental crowns and it refers specifically to the forms or molds for use in making such cores, to the manner of preparation of the teeth and the manner of forming the cores after placement of the forms on the teeth.

This is an important matter insofar as it improves the appearance of the person who has a damaged tooth, and requires the crown work to be done. It is also important for the health of that person.

When a dentist decides to construct a crown, whether for an anterior tooth or for a posterior tooth, it is usually because tooth substance has been lost. Before he proceeds, however, he is faced with a dilemma in that the greatest part of this tooth substance must be replaced and the tooth prepared to provide retention and resistance for the intended crown. This involves placing a core on or about the tooth.

The quality and success of the core is crucial to the success of the crown. Placement of the core material is an awkward procedure, and preparation of the core places substantial demands on the skill of the operator. It can, in fact, be quite difficult.

Amongst many general practicing dentists there is still, today, a reluctance to undertake as much crown and bridge work as clinical considerations warrant. This is at least partly due to a lack of confidence in their clinical skills. Until now advances in dental materials and technology have not eased the demands on a dentist's manual ability in crown and bridge procedures.

An important object of this invention is to simplify one of the major clinical steps in crown construction and so make complex work a less daunting prospect for the broad dental community.

Another object is to shorten chairside time and to enhance the retention and stability of many crowns and bridges.

Yet another object is to provide a method of preparation of teeth for the reception of core forms such that the cores, when formed, will be securely attached to the respective teeth and will provide secure foundations for the attachment of the eventual crowns.

In addition, the invention provides an improved core form and an improved manner of making the core.

In accordance with the present invention there is provided a dental core form including a sleeve-like member to fit on a portion of a tooth on which a core for a crown is to be formed, and said sleeve-like member is corrugated longitudinally so that the core formed by the use of the core form will be externally circumferentially corrugated.

In order that the invention may be clearly understood and readily put into practical effect, preferred non-limitative embodiments of a dental core form constructed in accordance with the invention will now be described with reference to the accompanying drawings, in which.

Figure 1:
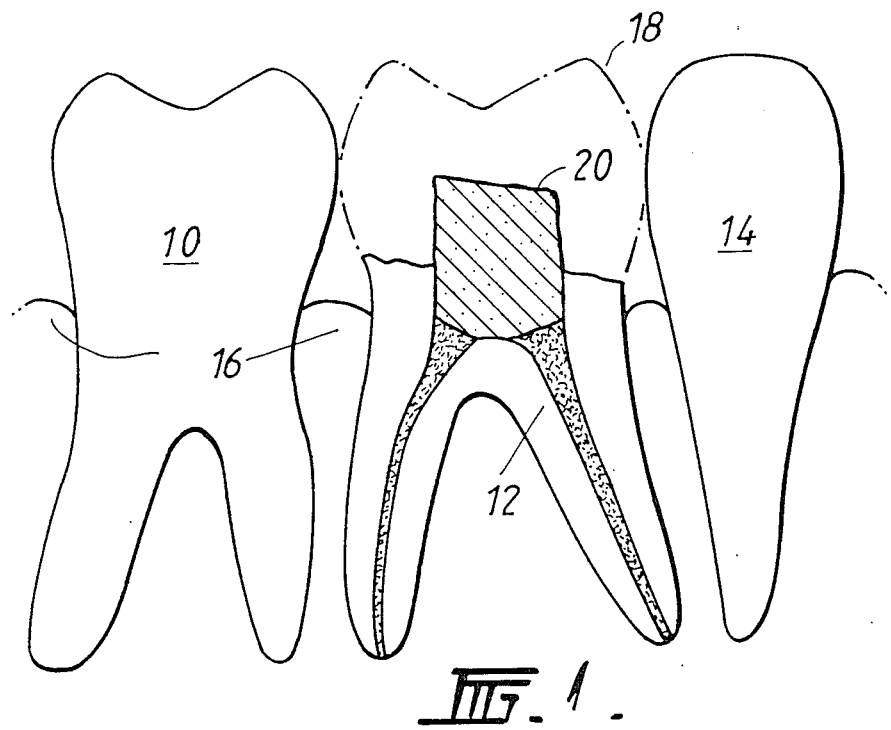
FIG. 1 is a partial cross-sectional view of teeth where the middle tooth requires restoration.

In FIG. 1 there is shown three lower posterior teeth 10, 12 and 14 seated in gum 16. Tooth 12 has lost its fitted crown 18 as indicated by the dashed lines, and requires fitting of a new crown. The old amalgam 20 must be removed and tooth 12 prepared for restoration. The invention is also suitable for restoration of decaying teeth or where extensive clinical loss has occurred.

Figures 2, 3:
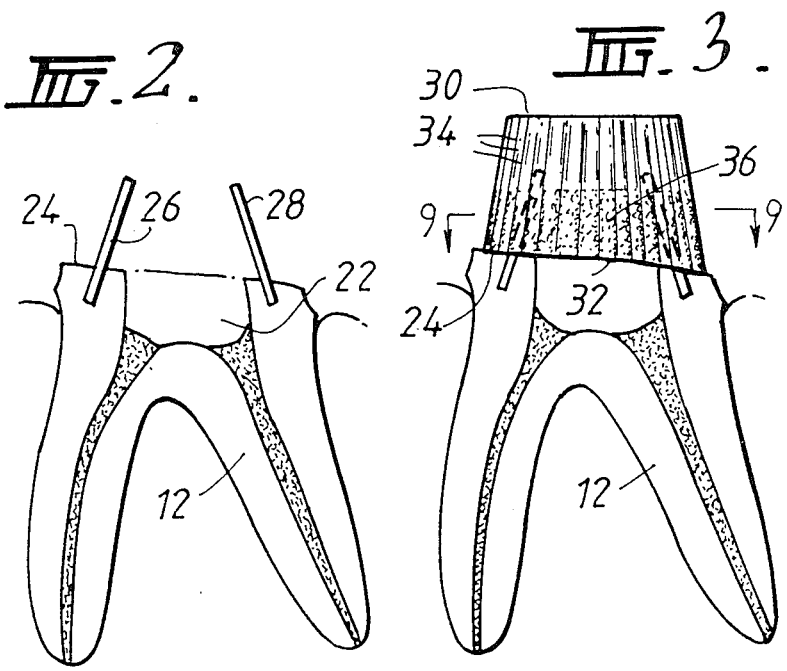
FIG. 2 is a cross-sectional view of the damaged tooth shown in FIG. 1 which has been prepared for restoration.
FIG. 3 is a view similar to FIG. 2 showing a first embodiment of a core form made in accordance with the invention positioned on the prepared tooth.

FIG. 2 shows tooth 12 having been prepared for restoration. The old amalgam has been removed and the access cavity 22 have been cleaned. The basal surface 24 of tooth 12 is cut to provide a relatively smooth surface for fitting a core thereon. Pins 26, 28 are secured in the stub of tooth 74 with portions thereof projecting outwardly from basal surface 28 into the space to be occupied by the core to be formed. Preferably pins 26, 28 are angled inwardly to provide a more secure fitting of the core. The tooth 12 is now ready to receive the core to be formed.

FIG. 3 shows a first embodiment of a core form 30 which has been slipped over the pins 26, 28 and positioned on basal surface 24. The core forms are made to suit the different types of teeth—molars, premolars, canines, and incisors, and—for each type—in a range of sizes. The base 32 of the selected core form 30 is shaped to match the basal surface 24 of tooth 12. It is to be noted that the core form 30, in carrying out this invention, should not project beyond the normal boundaries of the tooth but, rather, should be within those boundaries so that, when the crown is in place, the tooth will present a normal appearance as to size and shape. It is quite acceptable if the fit of the core form on the tooth is not quite perfect, as a small spacing at one or more locations will permit escape of core material during formation of the core and reduce the likelihood of air bubbles in the formed core.

Figure 9:
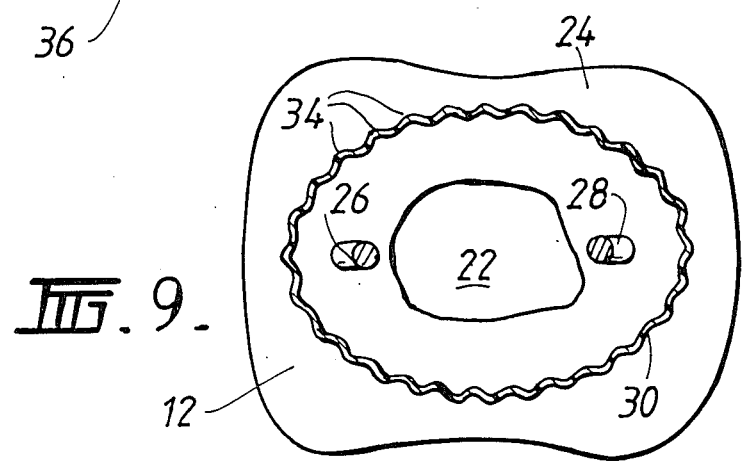
FIG. 9 is a cross-sectional view along and in the direction of arrows 9—9 of FIG. 3.

The core forms 30 are preferably made of synthetic plastics material, of transparent nature, which may be flexible or relatively rigid, as required. Core form 30 is corrugated in the longitudinal direction by flutes 34—extending in the vertical or longitudinal axis of the tooth. The core form is open at the base, so as to fit about the basal surface 28 of tooth 12 on which the crown is to be fitted, and also open at the top so as to surround the upper part of that tooth and provide an enclosure to receive the core material. As shown in FIG. 9 the core form is shaped to suit the shape of the tooth to which the crown is to be fitted. Accordingly the core form for an incisor tooth would be different from core form 30 for a molar tooth.

The core form should be such a lesser size than the tooth itself so that the form will fit about 1 mm to 1.5 mm in from the tooth's normal surface. Also, it is preferred that each form taper towards the occlusal or incisal, to an extent slightly more than that of the usual crown preparation, which has previously been on the basis of a very small taper, largely to make sure there are no undercuts. Typically the taper would be 1:5 for a molar and 1:7 for an incisor.

The effect of the corrugations in the form is to greatly increase the surface area of the core and thereby substantially increase the retention of the crown on the core and its stability thereon.

Once the correct style and size of core form 30 has been selected and shaped to fit on the prepared tooth 12 a small amount of composite resin is placed either at the margins of the form, or interproximally between the form and the neighbouring teeth. If the etching of enamel prior to the procedure is very brief, the composite resin will flick off later without any difficulty. It is important, however, that the material holds to the plastic of the form in the interim. This may be facilitated either by stippling the external surface of the plastic, and/or by placing a number of small protrusions or buttons on the surface.

Figures 4, 5:
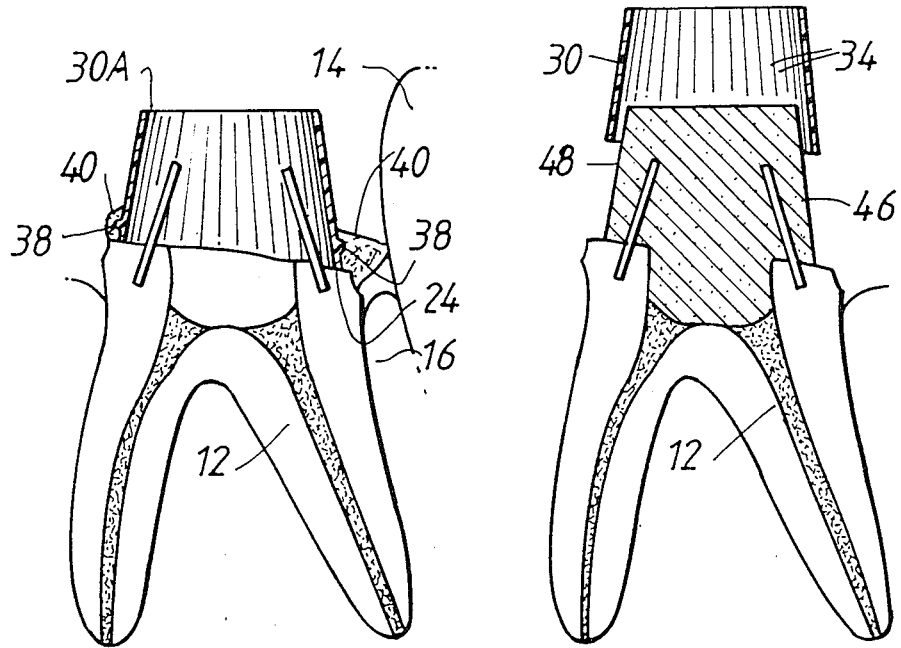
FIG. 4 shows a similar view to FIG. 3 using a second embodiment of a core form made in accordance with the present invention.
FIG. 5 shows a similar view to that of FIG. 3 with the core form being removed.

In FIG. 3 it can be seen that the lower portion of core form 30 has stippling or roughening 36 to assist in adhesion of the composite resin. FIG. 4 includes a plurality of protrusions 38 to which adhesive 40 is applied to lock core form 30A to teeth 10, 14 and to the basal surface 24. If required core form 30A may also include stippling or roughening.

Figure 7:
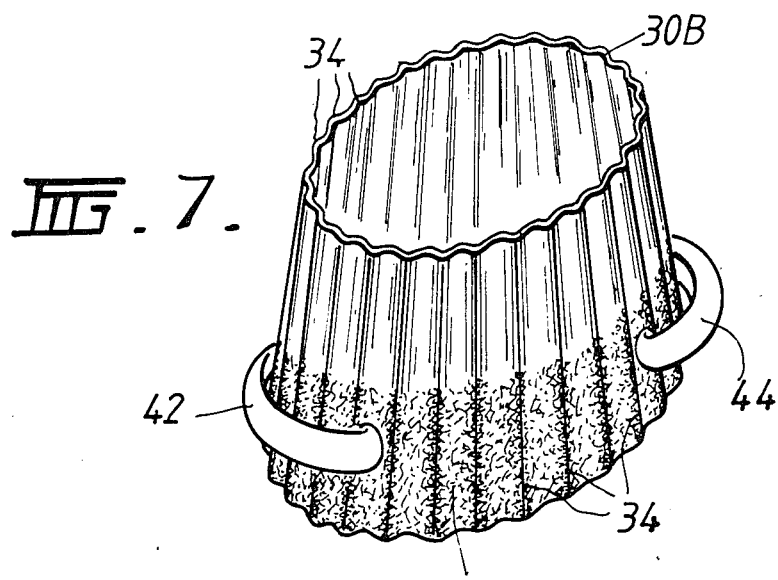
FIG. 7 is a perspective view of a third embodiment of a core form made in accordance with the present invention.
Figure 8:
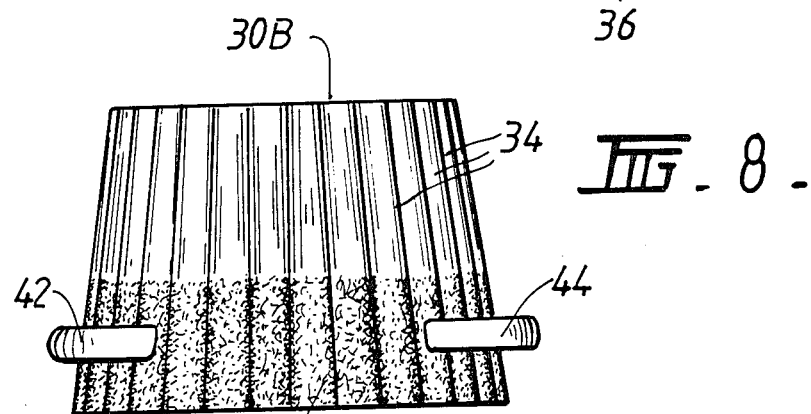
FIG. 8 is a side view of the core form shown in FIG. 7.

In the variation shown in FIGS. 7 and 8 handles 42, 44 are provided. With a little dab of adhesive these handles will be secured to teeth 10, 14 in order to prevent movement of core form 30B during filling with core material. Core form 30B shows more clearly the stippling or roughening 36 which will assist in increasing adhesion.

The core material 46—for example, the material known by the trade mark FULFIL—is now injected under force into core form 30, any excess material escaping around the margins being wiped away by using a plastic instrument, and the material cured. Core form 30 is removed as shown in FIG. 5. All that remains is for the occlusal height of the resultant core to be corrected, as by using a diamond bur.

The indications for the use of the core forms are the same as for a conventional clinical constructed core (as opposed to a laboratory cast core).

Figure 6:
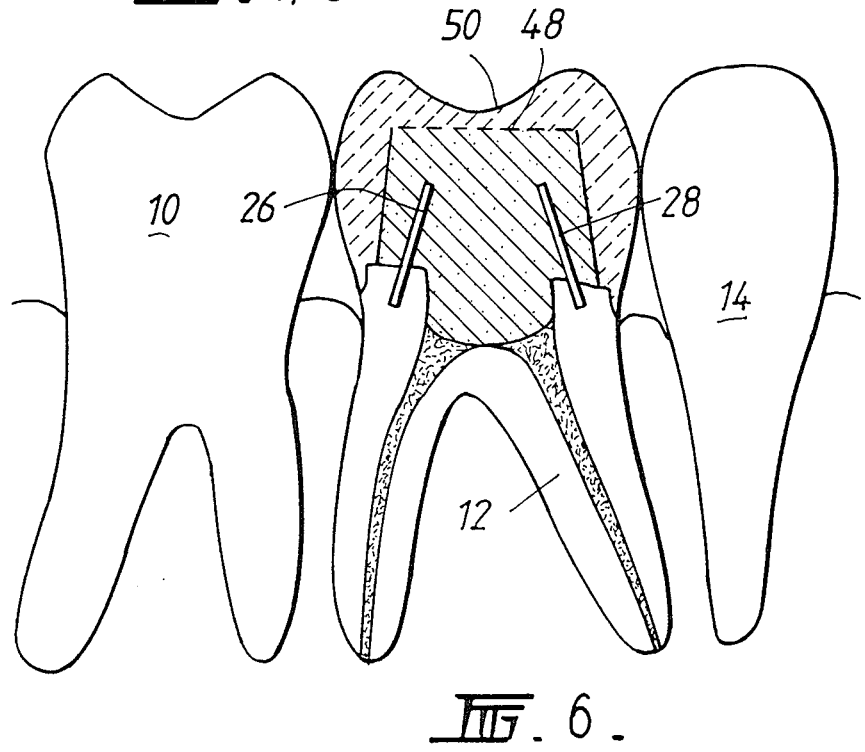
FIG. 6 is a similar view to that of FIG. 5 showing the fitting of a crown.

When the core has been correctly formed by use of this invention it should not require any further major preparation before the crown is fitted, and it should constitute a firm base for the crown. FIG. 6 shows the fitting of crown 50 to core 48 using known techniques.

An important feature of the invention resides in the provision of a core form adapted to fit about only that part of the tooth to which a crown is to be applied and to fit within the outline of the whole tooth so that when a crown is applied thereto it will not present a bulbous appearance. Another important feature is to provide a core form of corrugated shape so as to increase the surface area of the formed core, and thereby, the retention and stability of the crown on the core.

Yet another important preferred feature is the slightly accentuated taper, (greater than that of a traditionally prepare crown preparation), which the invention will impart to the core. This increased taper can be an advantage to the clinician in that it provides a wider range of paths of insertion of the crown between the adjacent neighbouring teeth. Likewise when two or more teeth act as abutments for a single structured bridge, the increased taper of their cores would greatly facilitate establishing a common path of insertion for the crown components of the bridge, despite the fact that these teeth may have very different axes.

Usually an increased taper in an otherwise traditionally prepared core is associated with low retention of the resultant crown. However, the corrugations which the invention will impart to the core and the resultant increase in surface area will more than compensate for the reduction in retention due to a slight increase in taper.

It is to be understood that many modifications in details of procedure may be made without departing from the ambit of the invention, the nature of which is to be ascertained from the foregoing description.

What is claimed is:

1. A dental core form including a sleeve-like member to fit about a portion of a tooth on which a core for a crown is to be formed, said sleeve-like member being tapered inwardly from the base to its outer end and being open at both ends, said core form having a maximum circumference which is less than that of the tooth with which it is to be used, said sleeve-like member being corrugated longitudinally so that the core formed by the use of the core form will be circumferentially corrugated, and at least an external portion of said sleeve-like member including means on a lower part thereof for assisting adhesive to secure said core form in the mouth during formation of said core.

2. A core form as claimed in claim 1, wherein said core form is formed from synthetic plastics material.

3. A dental core form as claimed in claim 1, wherein said means comprises a stippling or roughening of said lower part of said sleeve-like member.

4. A dental core form as claimed in claim 1, wherein said means comprises a plurality of outwardly extending protrusions.

5. A dental core form as claimed in claim 1, wherein said means comprises a plurality of handles.

6. A method of preparing a core for a crown on a tooth including the steps of:
 (a) preparing the tooth for receiving the core;
 (b) providing a dental core form by preparing a sleeve-like member to fit about a portion of the tooth so as to be tapered inwardly from its base to its outer end while being open at both ends and having a maximum circumference less than that of the tooth, corrugating the sleeve-like member longitudinally, and providing means on a lower part of the sleeve-like member for assisiting an adhesive to secure said core form in the mouth;
 (c) mounting said dental core form on the prepared tooth;
 (d) temporarily securing said core form by adhesive on said means to said prepared tooth or to an adjacent tooth;
 (e) fitting the core form with a hardenable material;
 (f) allowing the material to harden; and
 (g) removing the core form from the tooth and hardened material.

* * * * *